United States Patent
Jain et al.

(10) Patent No.: US 8,615,214 B2
(45) Date of Patent: Dec. 24, 2013

(54) METHOD AND SYSTEM FOR USING COMMUNICATION DEVICES FOR RETRIEVING PERSONAL MEDICAL DATA

(75) Inventors: Ashish Jain, Bridgewater, NJ (US);
Marc Pucci, Bridgewater, NJ (US);
John R. Wullert, II, Martinsville, NJ (US)

(73) Assignee: TTI Inventions C LLC, Wilmington, DE (US)

( * ) Notice: Subject to any disclaimer, the term of this patent is extended or adjusted under 35 U.S.C. 154(b) by 1187 days.

(21) Appl. No.: 12/187,156

(22) Filed: Aug. 6, 2008

(65) Prior Publication Data

US 2009/0047923 A1 Feb. 19, 2009

Related U.S. Application Data

(60) Provisional application No. 60/963,641, filed on Aug. 6, 2007.

(51) Int. Cl.
*H04M 11/04* (2006.01)
*H04W 4/00* (2009.01)

(52) U.S. Cl.
USPC ........................................ 455/404.1; 455/466

(58) Field of Classification Search
USPC ........... 455/404.1–404.2, 418–420, 410–411; 705/2–3
See application file for complete search history.

(56) References Cited

U.S. PATENT DOCUMENTS

| | | |
|---|---|---|
| 6,523,009 B1 | 2/2003 | Wilkins |
| 7,028,190 B2 | 4/2006 | Burakoff et al. |
| 7,039,628 B2 | 5/2006 | Logan, Jr. |
| 7,092,891 B2 * | 8/2006 | Maus et al. ......................... 705/2 |
| 7,213,266 B1 | 5/2007 | Maher et al. |
| 7,238,156 B1 | 7/2007 | Adamczyk |
| 7,328,276 B2 * | 2/2008 | Alisuag ........................... 709/237 |
| 7,490,048 B2 * | 2/2009 | Joao .................................. 705/3 |
| 7,725,332 B1 * | 5/2010 | Soong ............................... 705/3 |
| 2001/0049610 A1 * | 12/2001 | Hazumi ............................. 705/3 |
| 2001/0053987 A1 * | 12/2001 | Kleinschmidt et al. ............ 705/3 |
| 2002/0013520 A1 * | 1/2002 | Okamoto ....................... 600/300 |
| 2002/0120470 A1 | 8/2002 | Trice, Sr. |
| 2002/0178126 A1 * | 11/2002 | Beck et al. ....................... 705/75 |
| 2003/0037054 A1 * | 2/2003 | Dutta et al. .................... 707/100 |
| 2004/0203622 A1 * | 10/2004 | Esque et al. ................ 455/412.1 |
| 2005/0071194 A1 | 3/2005 | Bormann et al. |

(Continued)

OTHER PUBLICATIONS

"Telcordia Network Systems Family Leveraging the Power of Network Database & Toll Free Services for a Competitive Edge" Copyright 2000.

(Continued)

*Primary Examiner* — Brandon Miller
(74) *Attorney, Agent, or Firm* — Fitch, Even, Tabin & Flannery LLP

(57) ABSTRACT

The present invention discloses a method, system and a program storage device for remotely accessing medically relevant data stored on a server and provides remote access over a cellular or PCS communications network employing either a SMS or MMS communication protocol allowing dissemination of an individual's medically relevant data in an emergency, wherein the server authenticates each accessing PCS device by determining whether said accessing PCS device ID is stored in an emergency medical profile database and sending the user inputted emergency related personal data if the accessing PCS device ID is found in the emergency medical database device.

43 Claims, 3 Drawing Sheets

(56) References Cited

U.S. PATENT DOCUMENTS

| | | | |
|---|---|---|---|
| 2005/0114170 A1* | 5/2005 | Park et al. .......................... | 705/2 |
| 2005/0265326 A1* | 12/2005 | Laliberte ........................ | 370/389 |
| 2006/0128357 A1* | 6/2006 | Suryanarayana et al. . | 455/404.2 |
| 2006/0149597 A1 | 7/2006 | Powell et al. | |
| 2006/0230270 A1* | 10/2006 | Goffin ........................... | 713/173 |
| 2006/0293022 A1* | 12/2006 | Jindal et al. ................ | 455/404.1 |
| 2007/0061170 A1* | 3/2007 | Lorsch ............................ | 705/3 |
| 2007/0162308 A1* | 7/2007 | Peters ............................. | 705/2 |
| 2007/0250348 A1* | 10/2007 | D'Ambrosia et al. ............ | 705/3 |
| 2007/0263780 A1* | 11/2007 | Lentini ........................... | 379/37 |
| 2008/0021741 A1* | 1/2008 | Holla et al. ..................... | 705/3 |
| 2008/0177569 A1* | 7/2008 | Chen et al. ..................... | 705/2 |
| 2008/0200156 A1* | 8/2008 | Hicks et al. ................... | 455/415 |
| 2008/0233977 A1* | 9/2008 | Xu et al. ....................... | 455/461 |
| 2008/0288540 A1* | 11/2008 | Jarvis et al. ................ | 707/104.1 |
| 2009/0002145 A1* | 1/2009 | Berry et al. ................... | 340/436 |

OTHER PUBLICATIONS

International Search Report from related PCT/US08/72365, dated Nov. 7, 2008; 9 pages.

* cited by examiner

METHOD AND SYSTEM FOR USING COMMUNICATION DEVICES FOR RETRIEVING PERSONAL MEDICAL DATA

RELATED APPLICATIONS

This application claims the benefit of U.S. Provisional Application No. 60/963,641, entitled "Method and System for Using Cellular/Wireless Phones and Devices for Retrieving Emergency Related Personal Data," filed Aug. 6, 2007, which is hereby incorporated by reference.

FIELD OF INVENTION

The present invention relates generally to mobile personal communications services (PCS) and devices and more specifically, a method and system of retrieving medical information or other personal data by a PCS from a medical information system.

BACKGROUND OF THE INVENTION

Upon arriving on the scene of an accident or responding to some other life-threatening incident, emergency first-responders need access a victim's personal information in order to adequately assess the condition of and provide treatment to the victim. For example, first-responders might need to inquiry into a victim's medical history, and other emergency related personal details such as, age, blood type, medical allergies, past medical conditions, emergency contacts and the like. Needless to say, if the victim is incapacitated this information cannot be obtained, leaving first-responder to existing solutions, such as medical ID tags or searching through a victim's personal possessions to retrieve relevant data.

Other means of accessing medical records are known in the art such as providing portable health care histories that allows patients to carry the medical records with them. For example, U.S. Pat. No. 7,039,628, "Portable health care history information system," issued to Logan, describes a system that provides restricted access to a user's individual medical records through the use of a computer-readable identity card. Presumably, an identity card provides user identification from any location, that is, provided a computer and a card reader are readily available at the scene of the accident. Other examples of portable health care histories are taught in U.S. Pat. No. 6,523,009, "Individualized patient electronic medical records system," issued to Wilkins (patient records stored on CDROM or similar mobile storage device), and U.S. Patent Application 2002/0120470, "Portable personal and medical information system and method for making and using system" applied for by Trice (patient records on a memory stick with USB dongle attached to a key ring). While Logan, Wilkins and Trice may provide portable access to medical information, the information is unlikely to be up-to-date and could be lost or unavailable if the disk or other storage means is damaged.

Another scheme of accessing medical records involves remote access over a communications network, which could avoid the problem of staleness of medical data encountered by Logan, Wilkins and Trice. For example, U.S. Pat. No. 7,028,190, "Method and system for electronic delivery of sensitive information," issued to Burakoff et al describes a mechanism for requiring and providing consent prior to obtaining access to sensitive information, such as health records over an Internet connection (e.g. via e-mail). Burakoff's scheme presumes active consent, whereby the owner of the information must react to a request for access in order to indicate consent. This is not applicable in a situation where a user is incapacitated or otherwise impaired and therefore unable to provide consent.

An alternative approach utilizing a credential mechanism is taught in U.S. Pat. No. 7,213,266, "Systems and methods for managing and protecting electronic content and applications," issued to Maher, et al. which describes an approach for controlling the distribution of electronic content which relies on digital certificates to serve as the credentials and coordinates the content control through a certification service. While it would be possible to use this type of system to construct a remote medical history distribution mechanism, it would be impractical due to the high level of complexity.

Hence, there is a need for a method and system of remotely accessing medically relevant data over a communications network that is convenient and reliable yet secure in that it protects the privacy of the victim while disseminating an individual's medically relevant data in an emergency.

SUMMARY OF THE INVENTION

In one approach, a system is provided for remotely retrieving emergency related personal data. The system includes a secure user data input server, which is configured to create an emergency profile containing the emergency related personal data and link the emergency profile to one or more communication device IDs. The system further includes an emergency medical database device, which is configured to store the emergency profile and the one or more communication device IDs. The system next includes an emergency notification server connected to the emergency medical database device. The emergency notification server is configured to access the emergency profile and send the emergency related personal data to the accessing communication device in response to determining that the ID of the accessing communication device matches one of the one or more communication device IDs linked to the emergency profile.

In another approach, the system can further include a secure emergency responder data input server, which is configured to register one or more emergency responders, assign a responder code to the one or more emergency responders, and store the responder code in the emergency medical database device.

By one approach, a method is provided for remotely retrieving emergency related personal data. The method includes linking an emergency profile, which has the emergency related personal data, to an ID of a communication device. The method then stores the emergency profile in an emergency medical database device. Next, the method includes authenticating an accessing communication device attempting to access the emergency profile by determining whether an ID of the accessing communication device matches the ID of the communication device stored in the emergency medical database device. The emergency related personal data is then sent to the accessing communication device in response to determining that the ID of the accessing communication device matches the ID of the communication device stored in the emergency medical database device.

By another approach, the method can include registering an emergency responder on a secure emergency responder data input server, assigning a responder code to the emergency responder, linking the responder code to the emergency profile, and storing the responder code in the emergency medical database device.

In yet another approach, the method can include linking an ID of an emergency responder communication device to the emergency profile, and storing the ID of the emergency responder communication device in the emergency medical database device.

BRIEF DESCRIPTION OF THE DRAWINGS

The objects, features and advantages of the present invention will become apparent to one skilled in the art, in view of the following detailed description taken in combination with the attached drawings, in which.

DETAILED DESCRIPTION OF THE INVENTION

The present invention is directed to a system, method and program storage device for remotely accessing medically relevant data over a cellular or personal communications service (PCS) communications network utilizing communication protocols such as Short Message Services (SMS), Multimedia-Messaging Service (MMS) or the like. The SMS protocol is a popular feature of the global system mobile (GSM) standard which allows a subscriber to send short (up to 160 characters, including spaces) messages to other subscribers by entering the recipient's mobile phone number. Additional versions of SMS have been developed finding support in other mobile standards such as ANSI CDMA networks, Digital AMPS, as well as satellite networks and traditional landline implementations. The MMS protocol, like SMS, allows for the sending of text messages but also allows subscribers to include in these messages one or more multimedia parts (e.g. rich text, images, audio and video). In addition, both SMS and MMS have the ability to be managed by cellular or personal communications service (PCS) communications network providers through SMS or MMS gateways. For example, a gateway provider can facilitate SMS or MMS traffic between businesses and PCS devices and can identify the location of the PCS device. It should be noted that the present invention is not limited to cellular or PCS communication networks utilizing the SMS or MMS protocol. Other communication protocols such as unstructured supplementary services data (USSD), wireless application protocol (WAP), enhanced messaging service (EMS), an application-level extension to SMS, electronic mail communicated to and from a mobile device, text-capable paging systems, or even voice-telephony (using speech recognition and/or speech synthesis) can likewise be utilized by a cellular or PCS communication networks as known to those skilled in the art.

Figure 1:
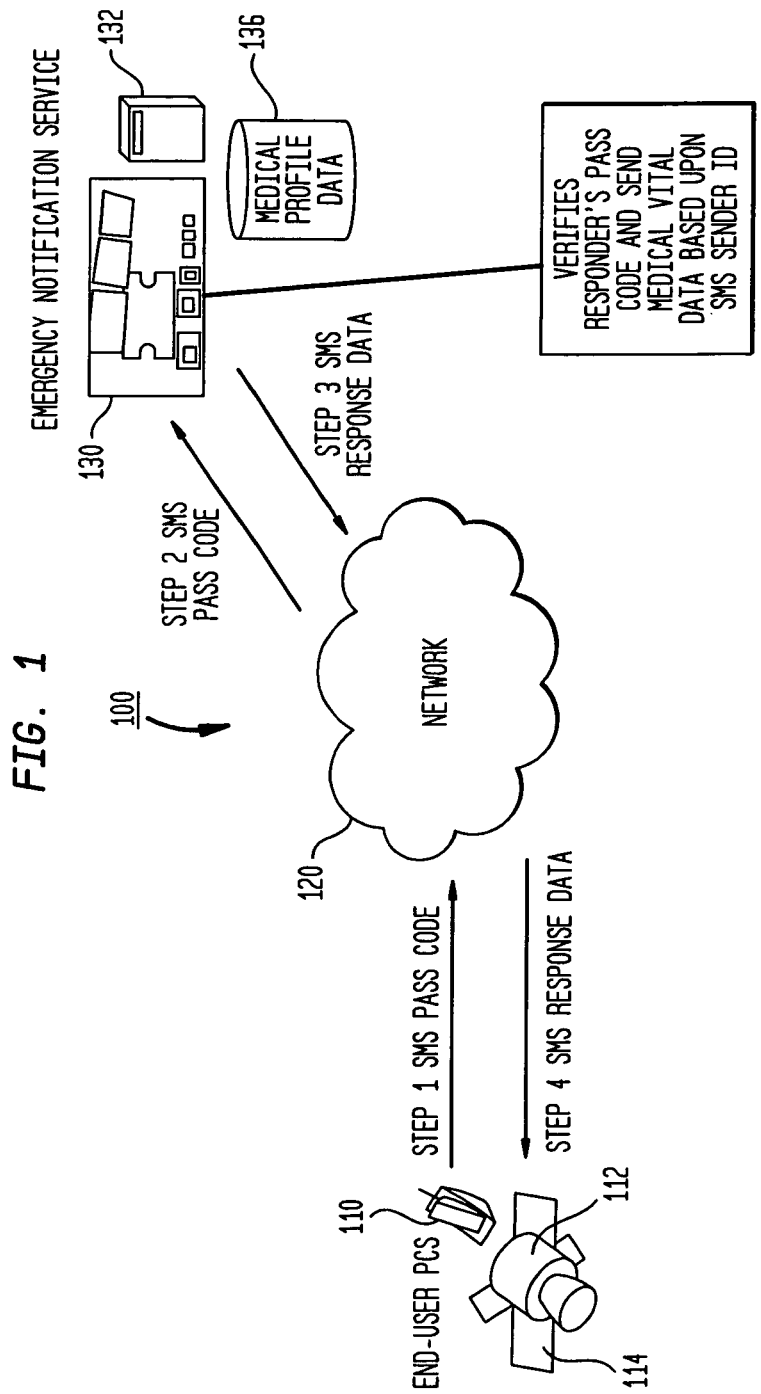
FIG. 1 illustrates a system and method of remotely accessing emergency related person data according to a first embodiment of the present invention.

Now referring to FIG. 1, a system and method 100 of remotely accessing emergency related personal data according to a first embodiment of the present invention is shown. As can be seen in FIG. 1, the system 100 includes an emergency notification service 130, such as Telcordia® Notification System or Telcordia® intelligent service control point (ISCP®), which is a computing system that interacts with network elements such as telephony switches, internet routers, SMS control centers to provide programmable control of how the connections or content delivery is achieved. The emergency notification service 130 provides a reliable delivery mechanism for notification of messages on a 24 hour, seven day a week, 365 days a year basis and includes an Internet connected server 132 for accessing medical records and for hosting a data input server (not shown). The data input server can be of any design known to those skilled in the art and will function to allow users to create one or more emergency medical data retrieval profiles to include such personal statistics as the person's age, blood type, known medical conditions and allergies, emergency contacts as well as the ability to upload an individual user's picture as more fully described below. In addition, the user would enter their cellular telephone number or PCS ID number to the data input server. The data input server would be password protected including any security method known to those skilled in the art. In addition, a storage device 136 is shown for storing each created emergency medical data retrieval profile.

The emergency notification service 130 also includes the functionality of a distributed network architecture, which would allow access to a plethora of medical databases such as hospital and doctor's office's medical databases. In other words, when a user creates an emergency medical data retrieval profile, they can give consent to allow access to their electronically maintained medical records from their hospital or doctor's office. Once a user consents to access, the emergency medical data retrieval profile can be periodically automatically updated with the user's most recent medical records from, for example, the user's most recent doctor's visit (without any additional interactions with the user or additional consent).

The system 100 as shown in FIG. 1 also includes an end user PCS device 110 and a cellular or PCS communication network 120 capable of supporting SMS and/or MMS or other functionally similar communication protocols.

Now the method of remotely accessing emergency related personal data according to a first embodiment of the present invention will be described. In the above-described system, a user creates one or more emergency medical data retrieval profiles by inputting emergency related personal data, which comprises the following three step.

First, a user creates one or more individualized emergency profiles by inputting the user emergency related personal data into a data input server. As mentioned above, a user will enter such personal statistics as the person's age, blood type, known medical conditions and allergies, and emergency contacts. The user might also be provided the ability to upload an individual user's picture as more fully described below. Other medically relevant data can be solicited as known to those skilled in the art. Moreover, the user can input the names of their doctors and any hospitals they frequent and will provide consent to accessing their medical records in accordance with Federal, state and local laws. The emergency notification service 130 as noted above, includes the functionality of a distributed network architecture, which would allow access to known medical databases maintained by a particular user's hospital and doctor's office's (if available). The specific design of the data input server is omitted and can be of any design including web pages making use of forms, dialog boxes and drop-down input inserts as known to those skilled in the art.

After inputting the personal statistics and other medically relevant data as well as health care professional information, the user will be prompted to provide a cellular number or PCS device ID. The cellular number or PCS device ID will link each one or more individualized emergency profiles to a user's PCS device, which can be a cellular telephone, personal digital assistant (PDA), an automobile telematic device or the like. Thereinafter, each one or more created and linked individualized emergency profiles are stored in storage device 132.

Then, after the individualized emergency profile is created and linked to a cellular number or PCS device ID, a user can now remotely access the individualized emergency profiles through a cellular or PCS communication network 120. As indicated above, both the end user PCS device 110 and cellular and PCS communication network 120 are capable of supporting SMS and/or MMS or other functionally similar communication protocols. Accordingly, as depicted in FIG. 1, an emergency first responder 112 can adequately and promptly gain access to the medical information of an end user accident victim 114 by using the end-user PCS 110 found in accident victim 114 possession to retrieve the victim's personal and medical information from the emergency notification service 130 in order adequately assess the condition of the victim.

As shown in FIG. 1, the accident victim 114 (if not incapacitated), emergency first responder 112 or other authorized person (not shown) can merely access the SMS application resident on the end-user PCS device 110 and input the well-known address of the emergency notification service 130 such as a telephone number or uniform resource locator address. As indicated in FIG. 1, end-user PCS device 110, in step 1 sends an SMS Pass Code to cellular and PCS communication network 120. In step 2, the cellular and PCS communication network 120 delivers the SMS Pass Code to the emergency notification service 130, which verifies that the cellular number or PCS device ID is stored in storage device 136 thus providing authentication to the emergency notification service and access by the end-user PCS device 110 to the previously created and linked emergency medical data retrieval profile. In addition, if the end-user PCS device 110 supports MMS, a picture of the registered PCS device owner previously stored in memory on storage device 136) can be sent from Internet connected server 132 to the end-user PCS device 110 to allow emergency first responder 112 to verify the identity of the accident victim 114. If multiple profiles are associated with the phone, such as if a husband and wife share a PCS device 110, the picture or other identifying information, such as gender and/or age, could be used by the first responder 112 to select the proper profile. Each attempt at access to the emergency notification service 130 will optionally be logged for each accessing end-user PCS device for later review and monitoring of unauthorized access.

An alternative embodiment would provide additional security to the sensitive personal information maintained by the emergency notification service 130, by requiring that the emergency first responder 112 input their EMT ID or other issued state or local ID in the body of the SMS text message which is stored either in the data in storage device 136 or accessible via the Internet to a network provider that maintains EMT ID or other issued state or local IDs.

Yet another alternative embodiment could require that the accident victim be conscious enough to utter a short key phrase which emergency first responder 112 would input into the body of the SMS message. In this case, the key phrase would be verified against information that was entered by the end user 110 during the registration phase and stored in the memory of the storage device 136. If a message was received with an incorrect key phrase, one option would be to send an error message in response, rather than the medical information. This would provide a higher degree of security, but would have the adverse consequence of preventing retrieval of information associated with a victim 114 who is incapacitated. By default, the method and system disclosed herein is configured based upon the assumption that the victim is not in a position to communicate with the first responder 112. In this embodiment if the first responder 112 is unable to elicit the short key phase, notification would nonetheless be sent to accident victims 114 emergency contact(s) previously associated to end-user device when he or she registered the PCS device. To provide notification to accident victim's 114 emergency contact(s), the present invention's Internet connected server 132 can be configured for accessing the plain old telephone service (POTS) network for automatically notifying accident victim's 114 emergency contacts anytime there is access to the emergency notification service. This option is not limited to this embodiment but can be a separate object of the invention.

After the end-user PCS device is authenticated, the emergency notification system 130 will in step 3, send accident victim 114 SMS Response Data obtained from the individual's emergency medical data retrieval profile back to the cellular and PCS communication network 120 which will finally route information to the end-user PCS 110 in step 4.

Figure 2:
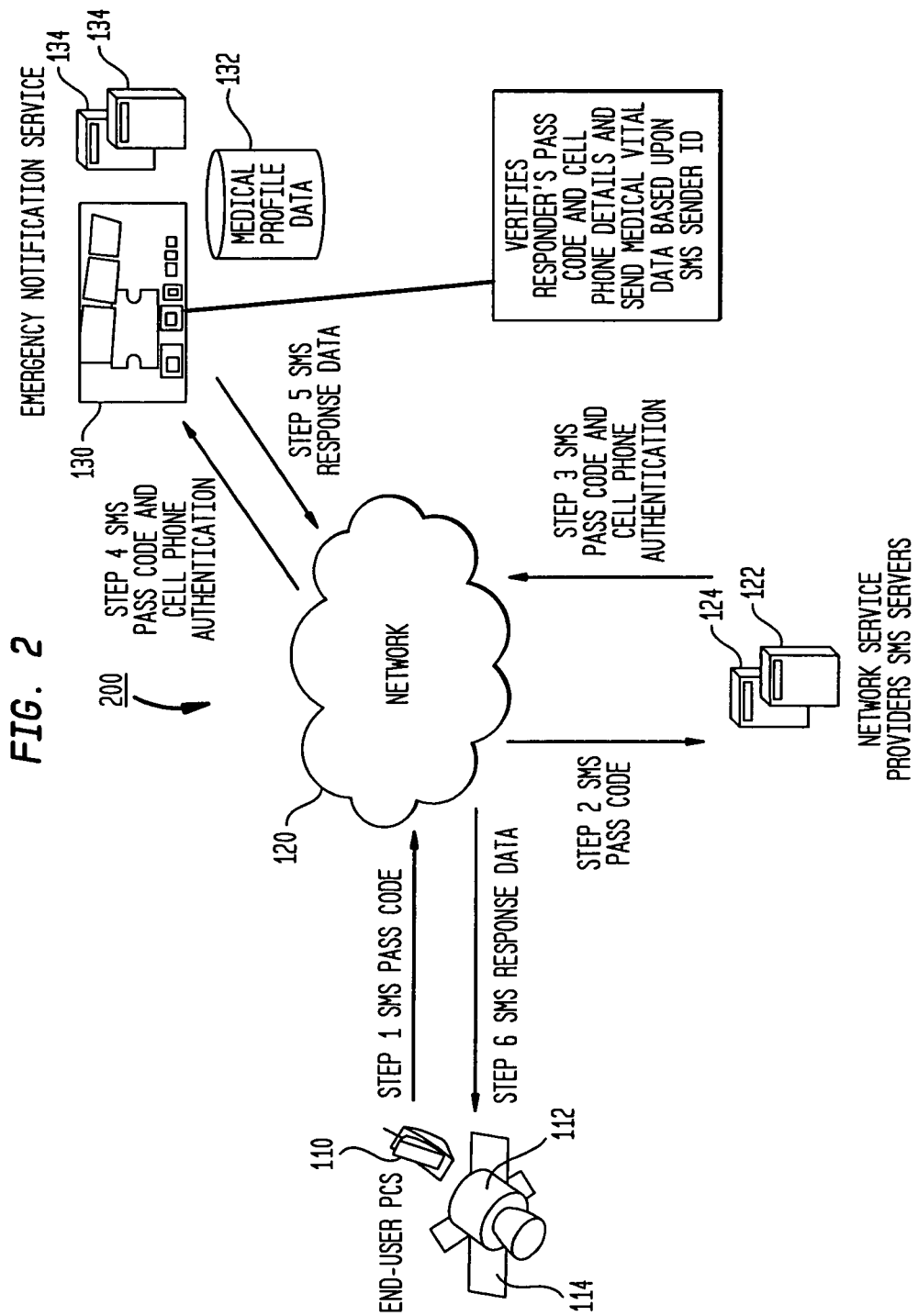
FIG. 2 illustrates a system and method of remotely accessing emergency related person data according to a second embodiment of the present invention.

Referring now to FIG. 2, a system and method of remotely accessing emergency related person data according to another embodiment of the present invention is shown. The system and method is similar to that shown in FIG. 1 with the exception of an additional responder server 134 provided in the emergency notification service 130 and inclusion of a network service providers' SMS gateway server 124 and ESN registration server 122. Network service providers are such providers as Verizon, T-Mobile, Cingular, Sprint, and the like.

As indicated above with respect to FIG. 1, as an added measure of security an emergency first responder 112 may be required to input their EMT ID code. However, if emergency first responder 112 does not have an EMT ID or other issued state or local ID, additional responder server 134 provides a data input server to allow registration and issuance of a responder pass code (prior to the accident) by requiring that a first responder input their name, affiliated fire department or other emergency first responder organization and other identifying information such as their date of birth. Moreover additional responder server 134 would provide a means for verifying and updating each assigned first responder code by a location, an affiliated trauma center ID, and a state or local EMT ID and the like and store this data in storage device 132.

In FIG. 2, network service providers' ESN registration server 122 is provided for restricting access to a SIM card ID or ESN ID number assigned to each end-user PCS device 110 in a cellular or PCS communications service 120. In other words, as known to those skilled in the art, the SIM card ID or ESN ID number can be dynamically linked to the emergency medical data retrieval profile to prevent unauthorized user access. Moreover, fraudulent SMS messages (messaged with headers spoofed) would be also identified using this process to improve security of the medical data.

Moreover, SMS gateway server 124 is provided for adding the functionality of determining the location of accident victims 114 end-under PCS 110 to assist in a search and rescue scenario. For example, if an accident victim's location is unknown, an emergency first responder 112 can access the location of the last cell tower encountered by the end-user PCS device 110.

Figure 3:
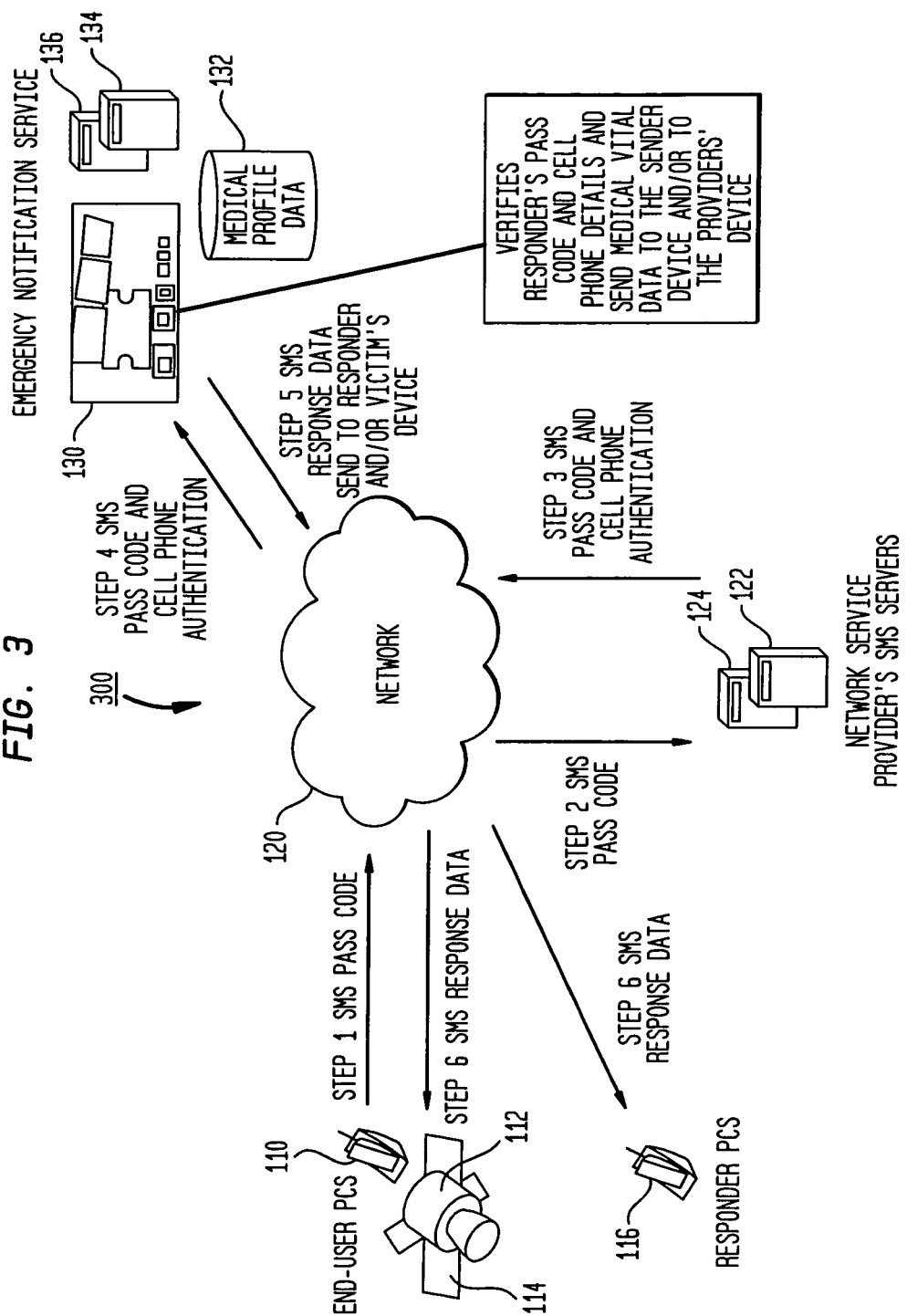
FIG. 3 illustrates a system and method of remotely accessing emergency related person data according to a third embodiment of the present invention.

Now referring to FIG. 3, a system and method of remotely accessing emergency related personal data according to another embodiment of the present invention is shown. In this embodiment, an emergency first responder 112 inputs his PCS device ID in a data input server (e.g. web page, interactive voice response system and the like) maintained on responder server 134, which stores that individual emergency responder's PCS ID in storage device 136. Accordingly, instead of sending an accident victim's emergency medical data retrieval profile to end-user PCS device 110 the emergency medical data retrieval profile is sent to responder's PCS device 116. In this embodiment of the invention an added level of security is provided to further protect against unauthorized access, whereas a victim's medically relevant data can only be accessed by an individual with possession of a victim's PCS device ID, knowledge of an EMT ID code and possession of a registered responder's PCS device linked to the EMT ID code.

Hence, the above described invention provides a novel system and method for providing remote access to medically relevant data over a communications network that is convenient and reliable yet secure in that it protects the privacy of the victim while disseminating an individual's medically relevant data in an emergency.

The present invention or aspects of the invention can also be embodied in a computer program product, which comprises all the respective features enabling the implementation of the methods described herein, and which—when loaded in a computer system—is able to carry out these methods. Computer program, software program, program, or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

The present invention can also be embodied as a program on a computer-readable recording medium. Examples of the computer-readable recording medium include but are not limited to Compact Disc Read-Only Memory (CD-ROM), Random-Access Memory (RAM), floppy disks, hard disks, and magneto-optical disks.

While there has been shown and described what is considered to be various specific embodiments of the invention, it will, of course, be understood that various modifications and changes in form or detail could readily be made without departing from the spirit of the invention. It is therefore intended that the scope of the invention not be limited to the exact forms described and illustrated, but should be construed to cover all modifications that may fall within the scope of the appended claims.

What is claimed is:

1. An apparatus comprising:
  a secure data input server configured to receive personal medical data to create a personal medical profile containing the personal medical data and link the personal medical profile to one or more user communication device IDs and one or more responder communication device IDs;
  a medical database device configured to store the personal medical profile, the one or more user communication device IDs, and the one or more responder communication device IDs;
  a notification server connected to the medical database device, wherein the notification server is configured to:
    access the personal medical profile;
    authenticate an accessing communication device by determining whether an ID of the accessing communication device matches one of the one or more user communication device IDs linked to the personal medical profile; and
    send the personal medical data to one or more responder communication devices associated with the one or more responder communication device IDs in response to determining that the ID of the accessing communication device matches one of the one or more user communication device IDs linked to the personal medical profile.

2. The apparatus of claim 1, wherein the accessing communication device is configured to access the notification server using a short message service and the one or more responder communication devices are configured to receive the personal medical data by short message service in response.

3. The apparatus of claim 1, wherein the personal medical data comprises at least one of an individual's age, blood type, medical allergies, medical conditions, emergency contacts information, or photograph.

4. The apparatus of claim 1, further comprising:
  a secure responder data input server configured to:
    register a responder;
    assign a responder code to the responder; and
    store the responder code in the medical database device.

5. The apparatus of claim 4, wherein the secure responder data input server is further configured to verify the responder code by at least one of a location, an affiliated trauma center ID, or a state or local medical technician ID and store the verified responder code in the medical database device.

6. The apparatus of claim 5, wherein the secure responder data input server is further configured to:
  issue a second responder code in response to receiving responder identification information associated with a non-verifiable responder;
  store the responder identification information and the second responder code in the medical database device; and
  authenticate a responder communication device having the second responder code by requiring input of the responder identification information.

7. The apparatus of claim 1, further comprising:
  a monitoring device configured to log access to the notification server for review of unauthorized access.

8. The apparatus of claim 1, wherein access to the notification server is restricted to accessing communication devices having a subscriber identity module card ID or electronic serial number ID assigned to the accessing communication devices by a communications service provider and predefined with the notification server.

9. The apparatus of claim 1 wherein the secure data input server is configured to receive the personal medical data information from at least a third party medical provider.

10. The apparatus of claim 9, wherein the personal medical data is configured to be dynamically updated by the third party medical provider to reflect recent events.

11. The apparatus of claim 1, wherein the notification server is further configured to authenticate accessing communication devices by requiring a pre-defined key phrase be included in a body of an accessing message.

12. The apparatus of claim 1, wherein the notification server is configured to be accessed at an address comprising a uniform resource locator or a telephone number.

13. The apparatus of claim 1, wherein the personal medical profile further comprises one or more emergency contacts and the notification server is further configured to notify the one or more emergency contacts in response to accessing the personal medical profile.

14. The apparatus of claim 13, wherein the notification server is further configured to send an accident notification message to the one or more emergency contacts, wherein the accident notification message provides the one or more emergency contacts at least one of a time or a location of the accessing communication device.

15. The apparatus of claim 1 wherein the secure data input server is configured to receive personal medical data from the user communication device.

16. A method comprising:
    receiving personal medical data to create a personal medical profile;
    linking the personal medical profile having the personal medical data to an ID of a user communication device and one or more responder communication device IDs;
    storing the personal medical profile in a medical database device;
    authenticating an accessing communication device attempting to access the personal medical profile by determining whether an ID of the accessing communication device matches the ID of the user communication device linked to the personal medical profile; and
    sending the personal medical data to one or more responder communication devices associated with the one or more responder communication device IDs in response to determining that the ID of the accessing communication device matches the ID of the user communication device stored in the medical database device.

17. The method of claim 16, wherein authenticating the accessing communication device and sending the personal medical data utilizes a short message service protocol.

18. The method of claim 16, wherein linking the personal medical profile having the personal medical data comprises linking a personal medical profile having personal medical data comprising at least one of an individual's age, blood type, medical allergies, medical conditions, emergency contacts information, or photograph.

19. The method of claim 16, wherein authenticating the accessing communication device further comprises:
    challenging the accessing communication device by requiring a key phrase in a body of a short message service message.

20. The method of claim 16, wherein authenticating the accessing communication device further comprises:
    receiving a short message service at an address comprising a uniform resource location or a telephone number.

21. The method of claim 16, further comprising:
    registering a responder on a secure responder data input server;
    assigning a responder code to the responder;
    linking the responder code to the personal medical profile; and
    storing the responder code in the medical database device.

22. The method of claim 21, wherein storing the responder code further comprises:
    verifying the responder code by at least one of a location, an affiliated trauma center ID, or a state or local medical technician ID; and
    storing the verified responder code in the medical database device.

23. The method of claim 21, further comprising:
    receiving responder identification information associated with a non-verifiable responder;
    issuing a second responder code;
    storing the responder identification information and the second responder code in the medical database device; and
    authenticating a responder communication device having the second responder code by requiring input of the responder identification information.

24. The method of claim 16, further comprising:
    logging accessing communication devices to monitor for unauthorized access.

25. The method of claim 16, further comprising:
    storing one or more emergency contacts in the medical database device; and
    notifying at least one of the one or more emergency contacts in response to an attempt to access the personal medical profile.

26. The method of claim 16, further comprising:
    restricting access to the personal medical profile to accessing devices having a subscriber identity module card ID or electronic serial number ID assigned to the accessing devices by a communications service provider and linked to the personal medical profile.

27. The method of claim 16 wherein receiving the personal medical data comprises receiving the personal medical data from at least a third party medical provider.

28. The method of claim 27, further comprising:
    dynamically updating the personal medical data by the third party medical provider to reflect recent events.

29. The method of claim 16, further comprising:
    receiving a location of the accessing communication device.

30. The method of claim 16 wherein receiving the personal medical data comprises receiving the personal medical data from the user communication device.

31. A tangible computer-readable medium having instructions stored thereon, the instructions configured to cause a computing device to perform operations comprising:
    receive personal medical data to create a personal medical profile having the personal medical data;
    link the personal medical profile to an ID of a user communication device and one or more responder communication device IDs;
    store the personal medical profile, the ID of the user communication device, and the one or more responder communication device IDs in a medical database device;
    authenticate an accessing communication device by determining whether an ID of the accessing communication device matches the ID of the user communication device stored in the medical database device; and
    send the personal medical data to one or more responder communication devices associated with the one or more responder communication device IDs in response to determining that the ID of the accessing communication device matches the ID of the user communication device stored in the medical database device.

32. The tangible computer readable medium of claim 31, wherein receive personal medical data comprises receive personal medical data from at least a third party medical provider.

33. An apparatus for remotely retrieving personal medical data, the apparatus comprising:
    a secure data input server configured to create a personal medical profile containing personal medical data and link the personal medical profile to one or more communication device IDs;
    a medical database device configured to store the personal medical profile and the one or more communication device IDs,
    a secure responder data input server configured to:
        register one or more responders;
        assign a responder code to the one or more responders;
        store the responder code in the medical database device;
        verify the responder code by at least one of a location, an affiliated trauma center ID, or a state or local medical technician ID and store the verified responder code in the medical database device;

issue a second responder code in response to receiving responder identification information associated with a non-verifiable responder;

store the responder identification information and the second responder code in the medical database device; and authenticate a responder communication device having the second responder code by requiring input of the responder identification information;

a notification server connected to the medical database device, wherein the notification server is configured to:

access the personal medical profile;

authenticate an accessing communication device by determining whether an ID of the accessing communication device matches one of the one or more communication device IDs linked to the personal medical profile; and send the personal medical data to the accessing communication device in response to determining that the ID of the accessing communication device matches one of the one or more communication device IDs linked to the personal medical profile.

34. A method for remotely retrieving personal medical data, the method comprising:

linking a personal medical profile having personal medical data to an ID of a communication device;

storing the personal medical profile in a medical database device;

registering a responder on a secure responder data input server;

assigning a responder code to the responder;

linking the responder code to the personal medical profile;

storing the responder code in the medical database device;

verifying the responder code by at least one of a location, an affiliated trauma center ID, or a state or local medical technician ID;

storing the verified responder code in the medical database device;

receiving responder identification information associated with a non-verifiable responder;

issuing a second responder code;

storing the responder identification information and the second responder code in the medical database device;

authenticating a responder communication device having the second responder code by requiring input of the responder identification information;

authenticating an accessing communication device attempting to access the personal medical profile by determining whether an ID of the accessing communication device matches the ID of the communication device linked to the personal medical profile; and sending the personal medical data to the accessing communication device in response to determining that the ID of the accessing communication device matches the ID of the communication device stored in the medical database device.

35. A method comprising:

accessing a database device having a personal medical profile stored thereon with a user communication device, the personal medical profile linked to a user ID and one or more responder communication device IDs and comprising personal medical data;

authenticating the user communication device by including a communication device ID while accessing the database device;

causing the personal medical data to be sent to one or more responder communication devices associated with the one or more responder communication device IDs in response to the communication device ID matching the ID linked to the personal medical profile.

36. The method of claim 35 wherein accessing the database device and utilizes a short message service protocol.

37. The method of claim 35 wherein causing the personal medical data to be sent to the one or more responder communication devices comprises causing at least one of an individual's age, blood type, medical allergies, medical conditions, emergency contacts information, or photograph to be sent to the one or more responder communication devices.

38. The method of claim 35 wherein authenticating the user communication device further comprises including a key phrase while accessing the database device, the key phrase being prestored and linked to the personal medical profile.

39. The method of claim 35 further comprising:

sending registration information to a server device;

receiving a responder code from the server device, the responder code stored in the database device and linked to the personal medical profile; and wherein authenticating the user communication device comprises including the responder code while accessing the database device.

40. The method of claim 39 further comprising sending verification information to the server device to verify the responder code, the verification information comprising a location, an affiliated trauma center ID, or a state or local medical technician ID.

41. The method of claim 35 further comprising:

sending non-verifiable responder identification information to a server device;

receiving a responder code from the server device, the responder code stored in the database device and linked to the personal medical profile; and wherein authenticating the user communication device comprises including the responder code and the non-verifiable responder identification information while accessing the database device.

42. The method of claim 35 further comprising sending personal medical data from the user communication device to be stored in the personal medical profile.

43. The method of claim 35 wherein the personal medical profile comprising personal medical data from at least a third party medical provider.

* * * * *